(12) United States Patent
Weber

(10) Patent No.: US 8,617,136 B2
(45) Date of Patent: Dec. 31, 2013

(54) BALLOON CATHETER DEVICES WITH DRUG DELIVERY EXTENSIONS

(75) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 468 days.

(21) Appl. No.: 12/858,796

(22) Filed: Aug. 18, 2010

(65) Prior Publication Data

US 2011/0054443 A1 Mar. 3, 2011

Related U.S. Application Data

(60) Provisional application No. 61/238,635, filed on Aug. 31, 2009.

(51) Int. Cl.
*A61M 31/00* (2006.01)
*A61M 29/00* (2006.01)

(52) U.S. Cl.
USPC ........ 604/509; 604/96.01; 604/104; 604/105; 604/106; 604/915

(58) Field of Classification Search
USPC .................. 604/509, 96.01, 101.01, 101.02, 604/103.01, 103.02, 103.05, 103.06, 604/103.07, 104, 105, 106, 915, 916, 97.01
See application file for complete search history.

(56) References Cited

U.S. PATENT DOCUMENTS 5,707,385 A * 1/1998 Williams ....................... 606/192
2006/0135985 A1 6/2006 Cox et al.

* cited by examiner

*Primary Examiner* — Kevin C Sirmons
*Assistant Examiner* — Shefali Patel
(74) *Attorney, Agent, or Firm* — Kenyon & Kenyon LLP

(57) ABSTRACT

A medical device is provided for dilatation of a vessel and delivery of a therapeutic agent to a wall of the vessel. The medical device comprises a catheter, a balloon located at a distal end of the catheter, and a drug delivery extension. The drug delivery extension is configured to extend beyond an outer surface of the balloon when the balloon is in an expanded configuration in order to deliver the therapeutic agent to an area beyond the outer surface of the balloon. The drug delivery extension may be one or more tubes, elongate members and/or expandable structures. The drug delivery extension may include a sheath for drug delivery.

20 Claims, 4 Drawing Sheets

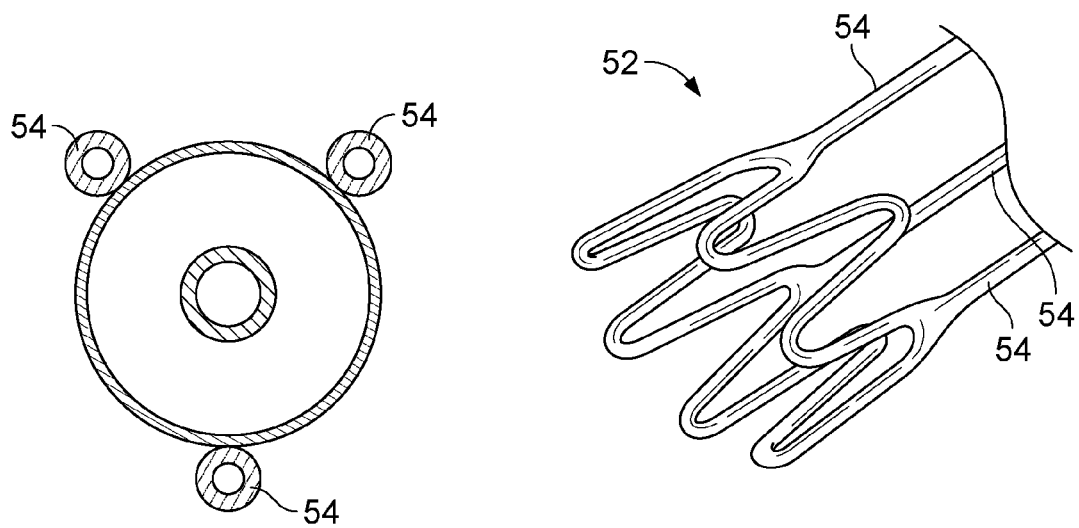
FIG. 9
FIG. 10
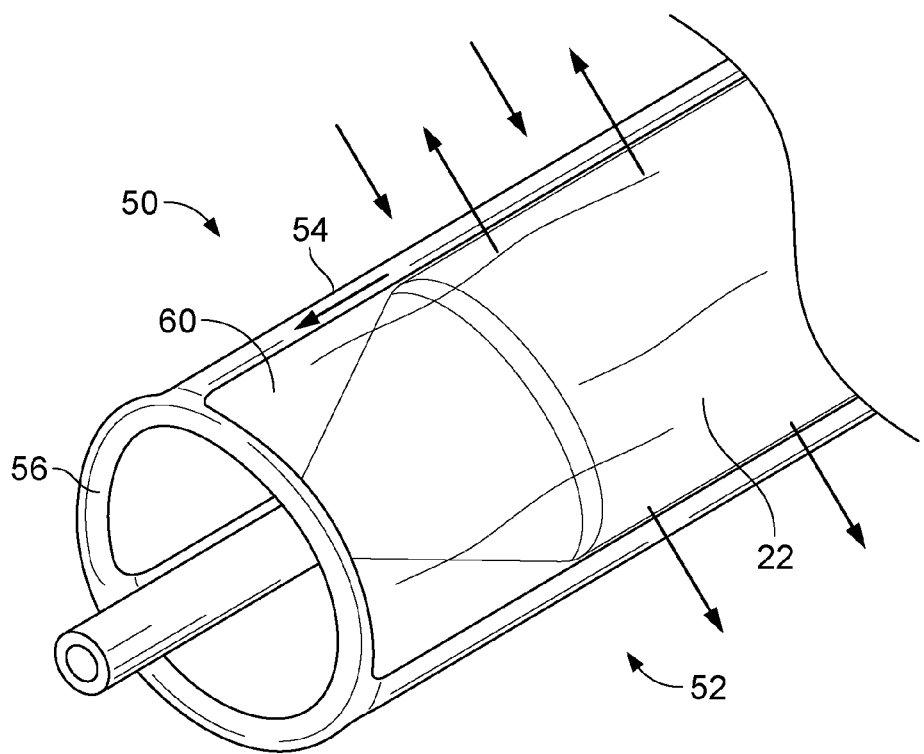
**FIG. 11

BALLOON CATHETER DEVICES WITH DRUG DELIVERY EXTENSIONS

RELATED APPLICATIONS

The present application claims priority to U.S. provisional application Ser. No. 61/238,635 filed Aug. 31, 2009, the disclosure of which is incorporated herein by reference in its entirety.

TECHNICAL FIELD

The present invention relates to medical devices, more particularly, to catheter devices.

BACKGROUND

Catheters are used in a wide variety of minimally-invasive or percutaneous medical procedures. Balloon catheters having drug coatings may be used to treat diseased portions of blood vessels. Typically, the balloon is inserted through a peripheral blood vessel and then guided via a catheter through the vascular system to the target intravascular site.

In many proposed drug delivery balloons, the balloon is similar to balloons that have been used in angioplasty procedures to dilate a stenosed region of a blood vessel. Such balloons have commonly been generally non-compliant balloons that can be inflated to relatively high inflation pressures without rupturing the blood vessel. In many proposed drug delivery balloons, the balloon is coated with or otherwise provided with drug on its outer surface. When the balloon is expanded at the area of the stenosis, the balloon not only opens the constriction as in a conventional angioplasty procedure but it also delivers drug to the area that is dilated by the balloon.

Despite the developments both with respect to balloon dilatation and drug delivery, there is a need for improvements in treatment devices and methods.

SUMMARY

In accordance with certain embodiments of the disclosure, a treatment device is provided in which the area of drug delivery extends beyond the area of balloon dilatation.

For example, in certain instances, it will be desirable that the area of drug delivery be different from the area of balloon dilatation. In certain instances, it may be desired that drug be delivered to one or more areas adjacent the area of balloon dilatation. It may be desired that this drug delivery to one or more areas adjacent the area of balloon dilatation be in combination with drug delivery to all or part of the area of balloon dilatation.

In one embodiment of the disclosure, a medical device is provided for dilatation of a vessel and delivery of therapeutic agent to a wall of the vessel. The medical device comprises a catheter, a balloon located at a distal end of the catheter, the balloon having a collapsed configuration and an expanded configuration, the balloon having an outer surface configured to press against the wall of the vessel when the balloon is expanded to its expanded configuration for dilatation of a constriction in the vessel, and a drug delivery extension. The drug delivery extension is configured to extend beyond the outer surface of the balloon when the balloon is in its expanded configuration in order to deliver the therapeutic agent to an area beyond the outer surface of the balloon. When the drug delivery extension is deployed, the drug delivery extension may extend, for example, distally from a distal end of the balloon in a direction generally parallel to a longitudinal axis of the balloon, proximally from a proximal end of the balloon in a direction generally parallel to a longitudinal axis of the balloon, or both distally and proximally. Additionally or alternatively, when the drug delivery extension is deployed, the drug delivery extension may extend away from the outer surface of the balloon in a direction extending away from the longitudinal axis of the balloon, for example for treatment of a side branch.

The drug delivery extension may comprise a tube having a rolled configuration and an unrolled configuration, wherein when the tube is in its unrolled configuration, the tube extends beyond the outer surface of the balloon in order to deliver the therapeutic agent to an area beyond the outer surface of the balloon. The medical device may further comprise a compression reservoir, wherein when the balloon is expanded to its expanded configuration and the compression reservoir is pressed by the balloon against the wall of the vessel, the compression reservoir is compressed to a compressed condition. Compression of the compression reservoir to its compressed condition causes the tube to unroll from its rolled configuration to its unrolled configuration. The compression reservoir may be a portion of the tube or a separate component. A plurality of tubes may be provided, each having a rolled configuration and an unrolled configuration.

The drug delivery extension may comprise an elongate member having a collapsed configuration and an expanded configuration, wherein when the elongate member is in its expanded configuration, the elongate member extends beyond the outer surface of the balloon in order to deliver the therapeutic agent to an area beyond the outer surface of the balloon. The medical device may further comprise an actuation mechanism for deploying the elongate member from its collapsed configuration to its expanded configuration. The actuation member may comprise a ring and/or one or more deployment wires. A plurality of elongate members may be provided, each having a collapsed configuration and an expanded configuration.

The drug delivery extension may comprise an expandable structure having a collapsed configuration and an expanded configuration, wherein when the expandable structure is in its expanded configuration, the expandable structure extends beyond the outer surface of the balloon in order to deliver the therapeutic agent to an area beyond the outer surface of the balloon. The medical device may further comprise a compression reservoir, wherein when the balloon is expanded to its expanded configuration and the compression reservoir is pressed by the balloon against the wall of the vessel, the compression reservoir is compressed to a compressed condition. Compression of the compression reservoir to its compressed condition causes the expandable structure to expand from its collapsed configuration to its expanded configuration. The compression reservoir may be a portion of the expandable structure or a separate component. The expandable structure may comprise a plurality of tubes, and the compression reservoir may comprise a portion of the tubes located on the outer surface of the balloon.

The therapeutic agent may be located on the outside of the drug delivery extension. For example, the therapeutic agent may be located on the outside of one or more tubes, on the outside of one or more elongate members, and/or on the outside of an expandable structure. Additionally or alternatively, the therapeutic agent may be located inside the drug delivery extension and may be forced out of openings in the drug delivery extension when the drug delivery extension is deployed. Additionally or alternatively, the medical device may further comprise a drug delivery sheath located on the outside of the drug delivery extension, wherein the therapeutic agent is located on the sheath, and wherein when the drug delivery extension is deployed, the drug is delivered from the sheath to the vessel wall.

As mentioned above, when the drug delivery extension is deployed, the drug delivery extension may extend distally from a distal end of the balloon, proximally from a proximal end of the balloon, or both distally and proximally. Also, as mentioned above, when the drug delivery extension is deployed, the drug delivery extension may extend generally radially outwardly from the outer surface of the balloon, for example for treatment of a side branch.

In another embodiment of the disclosure, a method for dilatation of a vessel and delivery of therapeutic agent to a wall of the vessel is provided, the method comprising: providing a medical device comprising: a catheter; a balloon located at a distal end of the catheter, the balloon having a collapsed configuration and an expanded configuration, the balloon having an outer surface configured to press against the wall of the vessel when the balloon is expanded to its expanded configuration for dilatation of a constriction in the vessel; and a drug delivery extension configured to extend beyond the outer surface of the balloon when the balloon is in its expanded configuration in order to deliver the therapeutic agent to an area beyond the outer surface of the balloon; delivering the balloon to the constriction in the vessel; expanding the balloon from its collapsed configuration to its expanded configuration such that the outer surface of the balloon presses against the wall of the vessel for dilatation of the constriction; and deploying the drug delivery extension to deliver the therapeutic agent to an area beyond the outer surface of the balloon. The medical device in the method may have one or more of the features described herein. The step of expanding the balloon from its collapsed configuration to its expanded configuration such that the outer surface of the balloon presses against the wall of the vessel may cause the deployment of the drug delivery extension.

BRIEF DESCRIPTION OF THE DRAWINGS

FIG. 9 shows a cross-sectional view of the medical device of FIG. 8 taken along the line 9-9 in FIG. 8.

FIG. 10 shows an enlarged view of an end region of the expansion structure of the medical device of FIG. 8.

FIG. 11 shows the medical device of FIG. 8 with the expansion structure in a deployed configuration.

DETAILED DESCRIPTION

Figure 1:
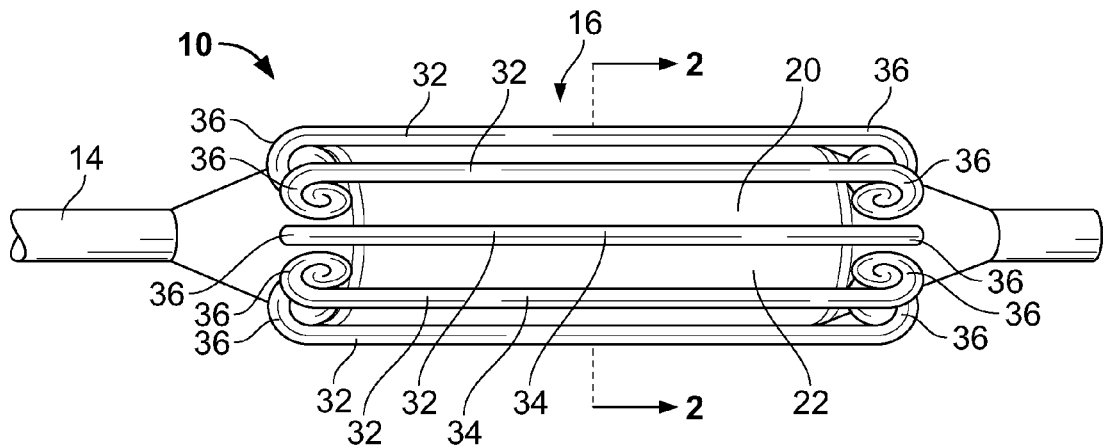
FIG. 1 shows a medical device according to an embodiment of the disclosure with a balloon in a collapsed configuration and a drug delivery extension comprising a plurality of tubes in an undeployed configuration.

FIG. 1 shows a medical device 10 according to one embodiment of the disclosure. The medical device 10 comprises a catheter 14 with a balloon 20 located at a distal end 16 of the catheter 14.

The catheter 14 and balloon 20 may be constructed and operated similarly to balloon catheters as known in the art, including but not limited to angioplasty catheters, stent delivery catheters, inflation catheters, and/or perfusion catheters. Any of various mechanisms conventionally used for the delivery, actuation, or expansion (e.g., by inflation) of balloon catheter devices may be used in conjunction with the catheter 14 and balloon 20. A lumen 18 may be provided through the balloon 20, for example for delivery of the balloon catheter over a guidewire and/or for perfusion purposes. The catheter devices of the present disclosure may be used in conjunction with other treatment or drug delivery devices, such as stents, as are known in the art.

Similar to conventional balloon catheters such as those known in the art, the balloon 20 has a collapsed configuration and an expanded configuration. FIG. 1 shows the balloon 20 in its collapsed configuration, while FIG. 3 shows the balloon 20 in its expanded configuration.

The balloon 20 has an outer surface 22 configured to press against the wall of a vessel when the balloon 20 is expanded to its expanded configuration. In this way, expansion of the balloon 20 can cause a dilatation of a constriction in the vessel, as in angioplasty procedures.

The medical device 10 has a drug delivery extension 30. The drug delivery extension 30 is configured to extend beyond the outer surface 22 of the balloon 20 when the balloon 20 is in its expanded configuration in order to deliver the therapeutic agent to an area beyond the outer surface 22 of the balloon 20. For example, as seen in FIG. 3, when the drug delivery extension 30 is deployed, the drug delivery extension 30 may extend distally from a distal end 26 of the balloon 20 and/or proximally from a proximal end 24 of the balloon 20.

Figure 2:
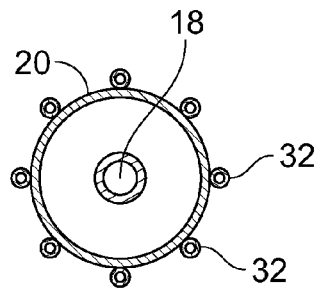
FIG. 2 shows a cross-sectional view of the medical device of FIG. 1 taken along the line 2-2 in FIG. 1.
Figure 3:
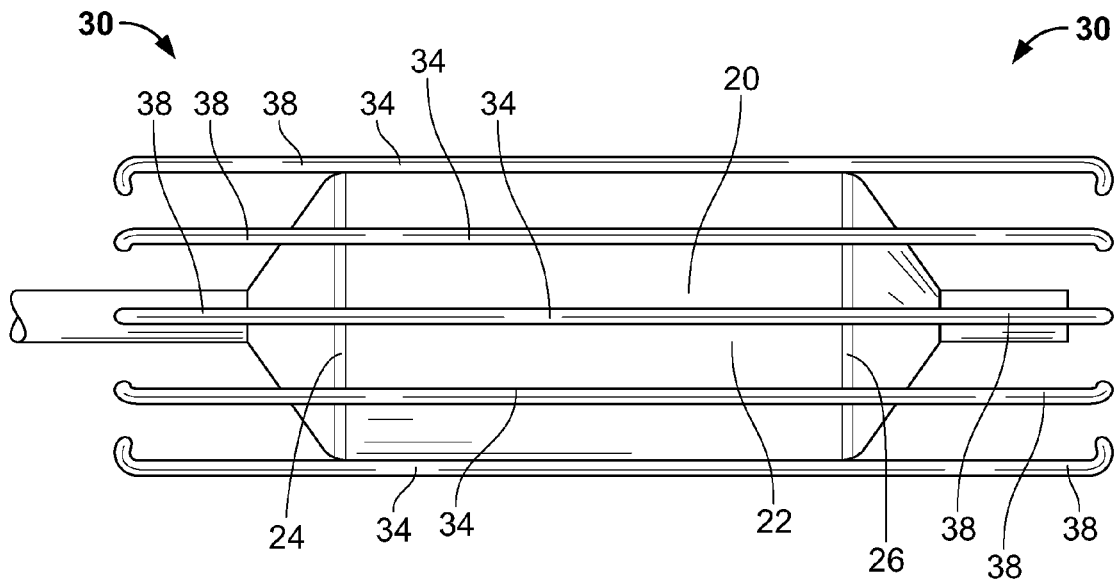
FIG. 3 shows the medical device of FIG. 1 with the balloon in an expanded configuration and the tubes in a deployed configuration.

In the embodiment illustrated in FIGS. 1-3, the drug delivery extension 30 comprises a plurality of tubes 32. Each tube 32 has an undeployed, rolled configuration, as shown in FIG. 1, and a deployed, unrolled configuration, as shown in FIG. 3. As can be seen in FIG. 3, when a tube 32 is in its unrolled configuration, the tube 32 extends beyond the outer surface 22 of the balloon 20, and, in this way, the tube 32 delivers therapeutic agent to an area beyond the outer surface 22 of the balloon 20. In the example illustrated in FIG. 3, when the drug delivery extension 30 is deployed, the drug delivery extension 30 extends in a generally longitudinal direction both distally from a distal end 26 of the balloon 20 and proximally from a proximal end 24 of the balloon 20.

In one example of an embodiment according to FIGS. 1-3, the tubes 32 may be filled with fluid and may be coated with, or may otherwise carry, a therapeutic agent. For example, the therapeutic agent may be coated on the tubes 32 in a polymer matrix. The fluid on the inside of the tubes 32 in this example is for purposes of deploying the tubes 32. In this example, the portion of each tube 32 extending along the outer surface 22 of the balloon 20 serves as a compression reservoir 34. When the balloon 20 is expanded, the pressure of the balloon 20 presses each compression reservoir 34 against the wall of the vessel, thereby compressing the compression reservoirs 34. This in turn forces fluid from the compression reservoirs 34 into the areas of the rolled sections 36. When this happens, the rolled sections 36 unroll to become unrolled sections 38 as shown in FIG. 3. Thus, when the balloon 20 is expanded to its expanded configuration and each compression reservoir 34 is pressed by the balloon 20 against the wall of the vessel, the compression reservoir 34 is compressed to a compressed condition. Compression of the compression reservoir 34 to its compressed condition causes the tube 32 to unroll from its rolled configuration to its unrolled configuration.

As shown in FIGS. 1-3, the drug delivery extension 30 may comprise a plurality of tubes 32, each having a rolled configuration and an unrolled configuration. As can be seen in the cross-sectional view of FIG. 2, eight tubes 32 are shown in this example, but more or fewer tubes 32 may be used. The tubes 32 may be any suitable size or shape and need not be circular in cross-section. For example, the cross-sectional shape of the tubes 32 may be oval, rectangular, square, or another suitable shape.

In the example shown in FIGS. 1-3, the portion of each tube 32 extending along the outer surface 22 of the balloon 20 extends in a longitudinal direction generally parallel to the longitudinal axis of the balloon 20. Other suitable configurations are possible. For example, the portion of each tube 32 extending along the outer surface 22 of the balloon 20 may extend in a generally helical direction around the outer surface 22 of the balloon 20. In this way, the length of this portion is increased. Since this portion becomes compressed upon balloon expansion and serves as the compression reservoir 34, it will be appreciated that having this portion be longer will result in more fluid being displaced, thereby increasing the ability to extend the drug delivery extension 30 beyond the outer surface 22 of the balloon 20.

In the example of FIGS. 1-3, the compression reservoir 34 is a portion of the tube 32 itself. Alternatively, a separate component, such as a compressible bladder or other structure, may be provided as the compression reservoir. Thus, for example, the compression reservoir may be provided on the outer surface 22 of the balloon 20, and the tubes may extend distally and/or proximally from the compression reservoir. In one example, the compression reservoir is a cylindrical sleeve around the outer surface 22 of the balloon 20, with tubes serving as the drug delivery extension and extending distally and proximally from the cylindrical sleeve. Additionally or alternatively, if desired, a non-compliant sheet or tube may be placed around the balloon 20 and the compression reservoir, whether the compression reservoir is a portion of a tube, a sleeve, or another suitable configuration. If the non-compliant sheet or tube is slightly smaller in diameter than the balloon 20, upon expansion of the balloon 20 the compression reservoir will be squeezed between the balloon 20 and the non-compliant sheet or tube. In this manner, the drug delivery extension may be deployed without the need for compressing the compression reservoir by pressure against the vessel wall.

As mentioned herein, the therapeutic agent may be located on the outside of the tubes 32. Additionally or alternatively, the therapeutic agent may be located inside the tubes 32 and may be forced out of openings in the tubes 32 when the tubes 32 are deployed. The therapeutic agent may form or be part of the fluid located in the tubes 32 for deployment of the tubes.

A medical device as described herein may be used in the following manner. First, the balloon, in its collapsed configuration, is delivered to the constriction in the vessel. Techniques such as those known in the art can be used to position the balloon at the desired site. Once the balloon is at the constriction, the balloon is expanded from its collapsed configuration to its expanded configuration. When sufficiently expanded, the outer surface of the balloon presses against the wall of the vessel for dilatation of the constriction. At or around this time, the drug delivery extension is deployed to deliver the therapeutic agent to an area beyond the outer surface of the balloon. In the example as described herein in which tubes 32 have compression reservoirs 34 that are compressed when the outer surface 22 of the balloon 20 presses the compression reservoirs 34 against the wall of the vessel, the step of expanding the balloon 20 to cause the outer surface 22 of the balloon 20 to press against the wall of the vessel also compresses the compression reservoirs 34 and causes the deployment of the drug delivery extension 30. In certain embodiments, increasing the pressure in the balloon 20 can cause an increased extension of the tubes 32, thereby allowing control of the length of the extension.

When the therapeutic agent is on the outside of the tubes 32, the unrolling of the tubes 32 causes the therapeutic agent to contact the vessel wall and thereby be delivered to areas of the vessel wall distally and/or proximally of the balloon 20. Similarly, when therapeutic agent is forced out of the interior of tubes 32 upon deployment of the tubes 32, such action also can cause the therapeutic agent to be delivered to areas of the vessel wall distally and/or proximally of the balloon 20.

Delivering therapeutic agent to an area beyond the outer surface of the balloon results in improved treatment for certain situations. For example, a blood vessel may have stenosis over a certain length, wherein a small section near the center of the length is heavily stenosed (e.g., greater than 70% stenosed) but the remainder of the length is not as heavily stenosed (e.g., less than 30% stenosed). It may be desired to dilatate only the heavily stenosed area, in order to avoid injury or other negative effects that might be associated with more extensive dilatation, or because of difficulties in accessing other areas for dilatation. However, while it may be desired to dilatate only the heavily stenosed area, it may be desired to deliver drug not just to the heavily stenosed area but also to adjacent areas. It may be desired to deliver drug to adjacent areas because, for example, dilatation of the heavily stenosed area can lead to restenosis over a longer area. Drugs may be delivered to the dilatation area and an adjacent area to promote healing or to prevent restenosis over a longer area, or for other reasons known in the art for which drugs are delivered in the area of a balloon dilatation. It will be appreciated that a medical device such as that described herein with a drug delivery extension to deliver therapeutic agent to an area beyond the outer surface of the balloon can achieve this goal of dilation over a first area with drug delivery over a second area.

The drug may be delivered not only to an area beyond the outer surface of the balloon but also to all or part of the area of balloon dilatation. This may be accomplished in ways known in the art, e.g., by coating the balloon, or by ways described herein, e.g., by drug delivery from tubes extending along the outer surface of the balloon. In certain instances, it may be desired that the drug be delivered only to an area beyond the outer surface of the balloon, which can also be accomplished with a device as described herein. In cases in which a drug coated stent is placed using the balloon, the balloon itself may be needed to deliver drug only to areas beyond that at which the stent is being placed. This may be include areas along the balloon surface where the stent is not located as well as areas beyond the balloon surface.

As mentioned herein, in a medical device 10 like that shown in FIGS. 1-3, when the tubes 32 are deployed, the tubes 32 may extend distally from the distal end 26 of the outer surface 22 of the balloon 20, proximally from a proximal end 24 of the outer surface 22 of the balloon 20, or both distally and proximally. In the embodiment illustrated in FIGS. 1-3, the tubes 32 extend in a direction generally parallel to a longitudinal axis of the balloon 20 both distally from the distal end 26 of the outer surface 22 of the balloon 20 and proximally from a proximal end 24 of the outer surface 22 of the balloon 20. Additionally or alternatively, when the drug delivery extension is deployed, the drug delivery extension may extend away from the outer surface 22 of the balloon 20 in a direction extending generally away from the longitudinal axis of the balloon 20.

Figure 4:
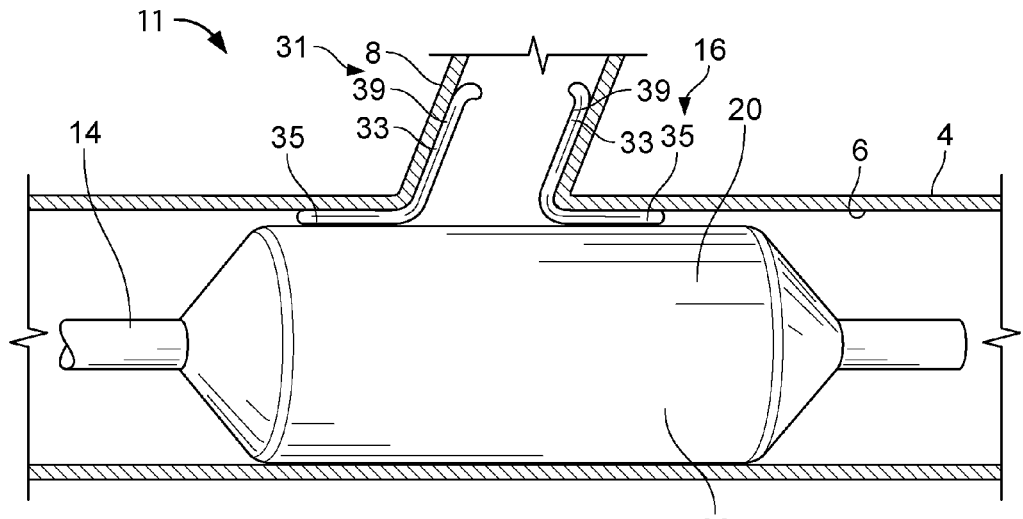
FIG. 4 shows a medical device according to another embodiment of the disclosure with a balloon in an expanded configuration and a drug delivery extension comprising a plurality of tubes in a deployed configuration, the tubes extending beyond the outer surface of the balloon in a direction generally radially outwardly from the outer surface of the balloon.

FIG. 4 shows an example of such a medical device wherein the drug delivery extension extends away from the outer surface of the balloon in a direction extending generally away from the longitudinal axis of the balloon. FIG. 4 shows a medical device 11 according to another embodiment of the disclosure. The medical device 11, like that in FIGS. 1-3, comprises a catheter 14 with a balloon 20 located at a distal end 16 of the catheter, which may be similar to the catheter 14 and balloon 20 as described with respect to FIGS. 1-3.

In FIG. 4, the medical device 11 has a drug delivery extension 31 comprising a plurality of tubes 33. The drug delivery extension 31 is configured to extend away from the outer surface 22 of the balloon 20 when the balloon 20 is in its expanded configuration in order to deliver the therapeutic agent to an area beyond the outer surface 22 of the balloon 20. For example, as seen in FIG. 4, when the drug delivery extension 31 is deployed, the drug delivery extension 31 extends away from the outer surface 22 of the balloon 20 in a direction extending generally away from the longitudinal axis of the balloon 20.

In the embodiment illustrated in FIG. 4, similar to the embodiment of FIGS. 1-3, the drug delivery extension 31 comprises a plurality of tubes 33. Each tube 33 has an undeployed, rolled configuration (not shown, but similar to the rolled configuration as shown in FIG. 1), and a deployed, unrolled configuration, as shown in FIG. 4. As can be seen in FIG. 4, when a tube 33 is in its unrolled configuration, the tube 33 extends away from the outer surface 22 of the balloon 20, and, in this way, the tube 33 delivers therapeutic agent to an area beyond the outer surface 22 of the balloon 20.

Similar to the drug delivery extension described herein with reference to FIGS. 1-3, the tubes 33 may be filled with fluid and may be coated with, or may otherwise carry, a therapeutic agent. In this example, a portion of each tube 33 extending along the outer surface 22 of the balloon 20 serves as a compression reservoir 35. When the balloon 20 is expanded, the pressure of the balloon 20 against the vessel wall causes compression of the compression reservoirs 35. This in turn forces fluid from the compression reservoirs 35 into the areas of the rolled sections. When this happens, the rolled sections unroll to become unrolled sections 39 as shown in FIG. 4. Thus, when the balloon 20 is expanded to its expanded configuration and the outer surface 22 of the balloon 20 presses against the wall 6 of the vessel 4, the compression reservoir 35 is compressed to a compressed condition. Compression of the compression reservoir 35 to its compressed condition causes the tube 33 to unroll from its rolled configuration to its unrolled configuration.

The medical device 11 shown in FIG. 4 is shown being deployed at a bifurcation of the vessel 4 having a side branch 8. The tubes 33 of the drug delivery extension 31, when deployed, can extend into the side branch 8 to deliver therapeutic agent into the side branch 8.

While only two tubes 33 are shown in FIG. 4, it will be appreciated that the medical device 31 may comprise a series of tubes 33 to extend around the inner periphery of the side branch 8. The tubes may be varied in number, size and/or shape as described herein. Alternatively, the drug delivery extension need not be one or more tubes but can instead be a suitable structure designed to deliver therapeutic agent to an area beyond the outer surface 22 of the balloon 20. For example, the drug delivery structure can be a single tube having a diameter approximating that of the side branch.

In a similar manner to that described in connection with FIGS. 1-3, the portion of each tube 33 extending along the outer surface 22 of the balloon 20 may have various configurations (e.g., straight, helical, etc.). Additionally, the compression reservoir 35 may be a portion of the tube 33 itself or a separate component, as described herein. Also, the therapeutic agent may be located on the outside of the tubes 33 or on the inside the tubes 33 and may be deployed as described herein.

A medical device like that shown in FIG. 4 can be used in a similar manner to that described herein with reference to FIGS. 1-3. The balloon, in its collapsed configuration, is delivered to the constriction in the vessel. Techniques such as those known in the art can be used to position the balloon at the desired site, adjacent the side branch. The balloon is expanded for dilatation of the constriction. At or around this time, the drug delivery extension is deployed to deliver the therapeutic agent into the side branch, beyond the outer surface of the balloon. In the example as shown in FIG. 4 in which tubes 33 have compression reservoirs 35 that are compressed when they are pressed by the balloon 20 against the wall 6 of the vessel 4, the step of expanding the balloon 20 to cause the outer surface 22 of the balloon 20 to press against the wall 6 of the vessel 4 also compresses the compression reservoirs 35 and causes the deployment of the drug delivery extension 31 into the side branch 8.

When the therapeutic agent is on the outside of the tubes 33, the unrolling of the tubes 33 causes the therapeutic agent to contact the vessel wall and thereby be delivered to areas of the vessel wall in the side branch. Similarly, when therapeutic agent is forced out of the interior of tubes 33 upon deployment of the tubes 33, such action also can cause the therapeutic agent to be delivered to areas of the vessel wall in the side branch.

Figure 5:
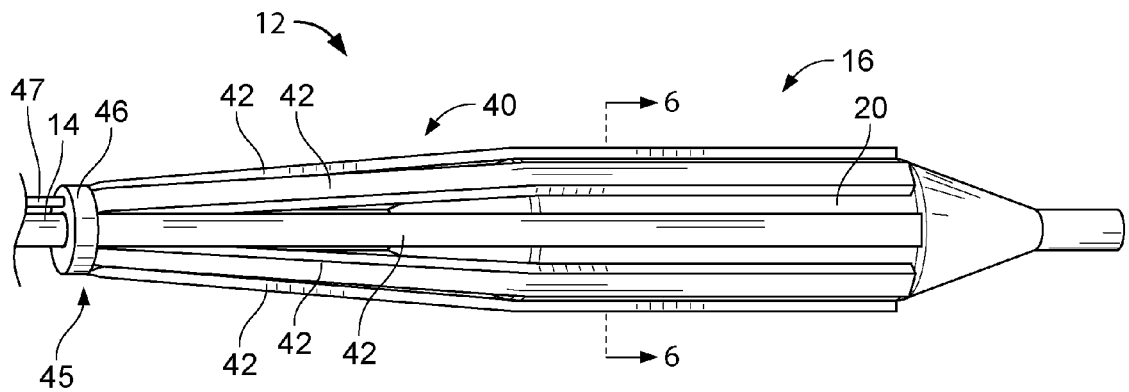
FIG. 5 shows a medical device according to another embodiment of the disclosure with a balloon in a collapsed configuration and a drug delivery extension comprising a plurality of elongate members in an undeployed configuration.
Figure 6:
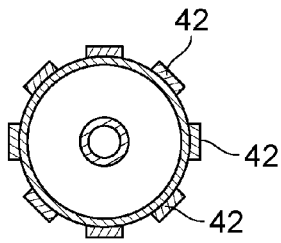
FIG. 6 shows a cross-sectional view of the medical device of FIG. 5 taken along the line 6-6 in FIG. 5.
Figure 7:
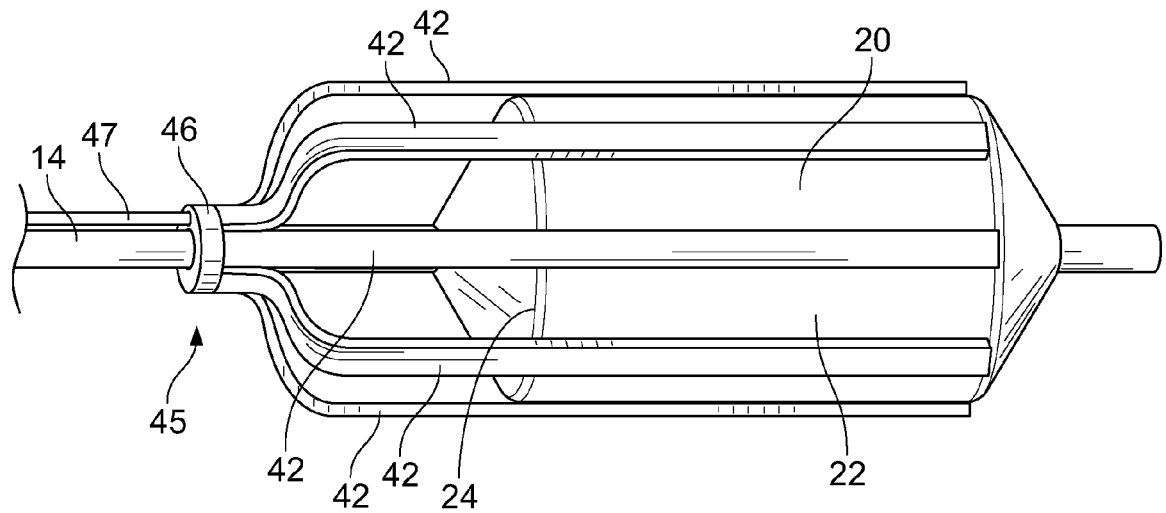
FIG. 7 shows the medical device of FIG. 5 with the balloon in an expanded configuration and the elongate members in a deployed configuration.

FIGS. 5-7 show a medical device 12 according to another embodiment of the disclosure. The medical device 12, like that in FIGS. 1-3, comprises a catheter 14 with a balloon 20 located at a distal end 16 of the catheter 14, which may be similar to the catheter 14 and balloon 20 as described herein in connection with FIGS. 1-3.

In FIGS. 5-7, the medical device 12 has a drug delivery extension 40 comprising a plurality of elongate members 42 configured to extend beyond the outer surface 22 of the balloon 20 when the balloon 20 is in its expanded configuration in order to deliver the therapeutic agent to an area beyond the outer surface 22 of the balloon 20. In FIG. 7, when the drug delivery extension 40 is deployed, the drug delivery extension 40 extends proximally from a proximal end 24 of the outer surface 22 of the balloon 20.

In FIGS. 5-7, each elongate member 42 has an undeployed, collapsed configuration, as shown in FIG. 5, and a deployed, expanded configuration, as shown in FIG. 7. As can be seen in FIG. 7, when an elongate member 42 is in its deployed configuration, the elongate member 42 extends beyond the outer surface 22 of the balloon 20 and can expand to the wall of the vessel, and, in this way, the elongate member 42 can deliver therapeutic agent to an area of the vessel wall beyond the outer surface 22 of the balloon 20.

As can be seen in the cross-sectional view of FIG. 6, eight elongate members 42 are shown in this example, but more or fewer elongate members 42 may be used. The elongate members 42 may be of any suitable size or shape and need not be rectangular in cross-section. For example, the cross-sectional shape of the elongate members 42 may be oval, circular, square, or another suitable shape. The elongate members 42 may be overlapping in their collapsed state.

Similar to the tubes as described herein, the elongate members 42 may be coated with, or may otherwise carry, a therapeutic agent. In this manner, when the elongate members 42 are deployed to their expanded configuration as shown in FIG. 7 against the vessel wall, the therapeutic agent can be delivered to the vessel wall.

The medical device 12 shown in FIGS. 5-7 further comprises an actuation mechanism 45 for deploying the elongate members 42 from the collapsed configuration to the expanded configuration. The actuation member 45 in this embodiment comprises a ring 46 and a deployment wire 47.

In the undeployed condition, as illustrated in FIG. 5, the ring 46 is located at a proximal position distanced away from the balloon 20. In this position, the elongate members 42 are maintained in their collapsed configuration. To deploy the elongate members 42, the ring 46 in this embodiment can be moved distally toward the balloon 20, causing the elongate members 42 to bend outwardly to the expanded configuration, as shown in FIG. 7. The ring 46 may be moved by an operator causing deployment wire 47 to advance distally thereby causing the ring 46 to advance distally.

A medical device 12 such as that shown in FIGS. 5-7 may be used in the following manner. The balloon 20, in its collapsed configuration, is delivered to a constriction in the vessel. Techniques such as those known in the art can be used to position the balloon 20 at the desired site. Once the balloon 20 is at the constriction, the balloon 20 is expanded from its collapsed configuration to its expanded configuration. When sufficiently expanded, the outer surface 22 of the balloon 20 presses against the wall of the vessel for dilatation of the constriction. At or around this time, the drug delivery extension 40 is deployed to deliver the therapeutic agent to an area beyond the outer surface of the balloon. In the example of FIGS. 5-7, the operator can advance the deployment wire 47 distally, causing the ring 46 to advance distally, which moves the elongate members 42 to the expanded configuration.

In FIG. 7, when the therapeutic agent is on the outside of the elongate members 42, the expansion of the elongate members 42 against the vessel wall can cause the therapeutic agent to contact the vessel wall and thereby deliver therapeutic agent to areas of the vessel wall proximal to the balloon 20. A similar configuration may be used to deliver therapeutic agent distal to the balloon 20.

In certain situations, it may be desirable to utilize a drug delivery sheath located on the outside of the drug delivery extension. In the example of FIGS. 5-7, a drug delivery sheath may be located on the outside of the elongate members 42. The therapeutic agent can be located on the sheath, such that when the drug delivery extension is deployed, the drug is delivered from the sheath to the vessel wall.

FIGS. 8-11 show a medical device 13 according to another embodiment of the disclosure. The medical device 13, like other embodiments described herein, comprises a catheter 14 with a balloon 20 located at a distal end 16 of the catheter, which may be similar to the catheter and balloon as described with respect to FIGS. 1-3.

In FIGS. 8-11, the medical device 13 has a drug delivery extension 50 configured to extend beyond the outer surface 22 of the balloon 20 when the balloon 20 is in its expanded configuration in order to deliver the therapeutic agent to an area beyond the outer surface 22 of the balloon 20. In FIG. 11, when the drug delivery extension 50 is deployed, the drug delivery extension 50 extends proximally and/or distally from one or both ends of the outer surface 22 of the balloon 20.

Figure 8:
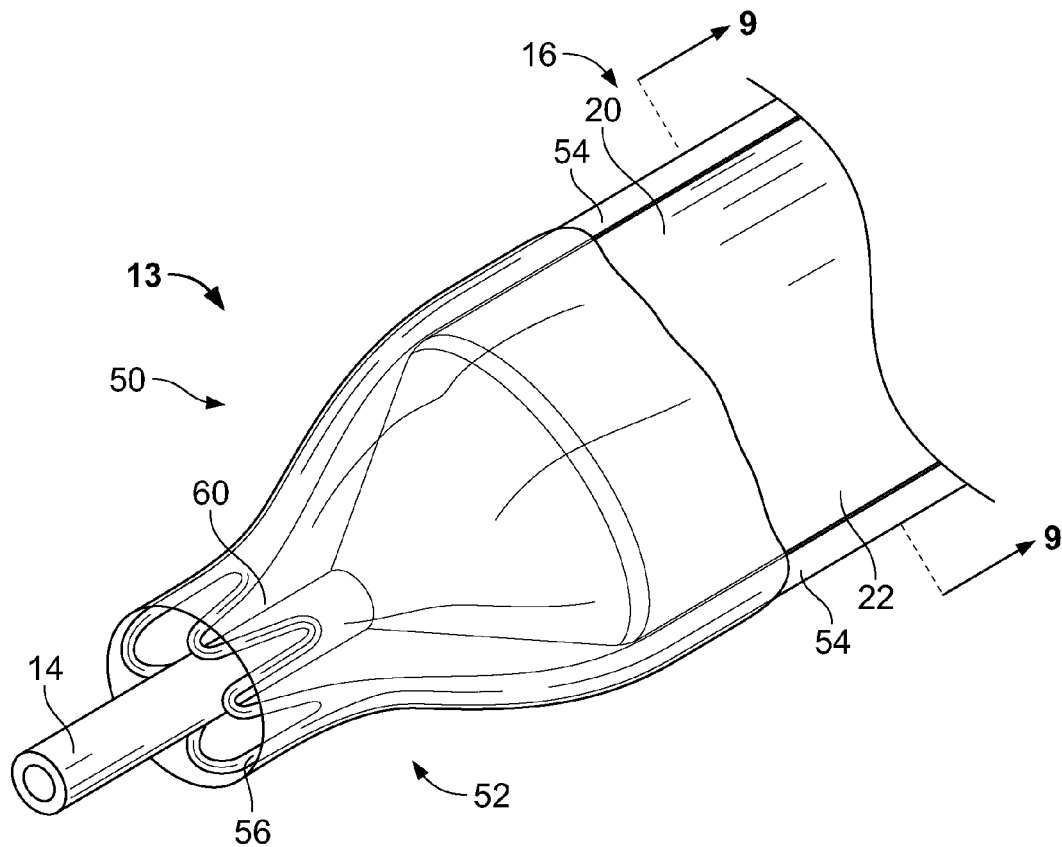
FIG. 8 shows a medical device according to another embodiment of the disclosure with a drug delivery extension comprising an expansion structure in an undeployed configuration.

In FIGS. 8-11, the drug delivery extension 50 comprises an expandable structure 52. The expandable structure 52 has a collapsed configuration, as shown in FIG. 8, and an expanded configuration, as shown in FIG. 11. As can be seen in FIG. 11, when the expandable structure 52 is in its deployed, expanded configuration, the expandable structure 52 extends beyond the outer surface 22 of the balloon 20, and, in this way, the expandable structure 52 delivers the therapeutic agent to an area beyond the outer surface 22 of the balloon 20.

The expandable structure 52 may be any suitable shape. In the example illustrated in FIGS. 8-11, the expandable structure 52 comprises a series of longitudinal elements 54 and expansion rings 56 (only one expansion ring 56 is illustrated, but it will be appreciated that an expansion ring 56 may be positioned proximal to the proximal end of the balloon and/or distal of the distal end of the balloon). In the unexpanded configuration, which is shown in FIG. 8 and in the enlarged end view of FIG. 10, the expansion rings 56 can have a generally wave-like configuration and a reduced diameter. In the expanded configuration, shown in FIG. 11, the expansion rings 56 are enlarged. The expansion rings 56 can then have a stretched out wave-like configuration with an extended wavelength or a generally circular configuration as shown in FIG. 11.

In the embodiment illustrated in FIGS. 8-11, the longitudinal elements 54 and expansion rings 56 of the expandable structure 52 are in the form of tubes filled with fluid, similar to tubes described herein with respect to FIGS. 1-3. In this form, the portions of the longitudinal elements 54 extending along the outer surface 22 of the balloon 20 can serve as a compression reservoir, as described herein with respect to FIGS. 1-3. When the balloon 20 is expanded to its expanded configuration and the compression reservoir is pressed by the balloon 20 against the wall of the vessel, the compression reservoir is compressed to a compressed condition, thereby forcing fluid into the expansion ring(s), causing the expandable structure 52 to expand.

As can be seen in the cross-sectional view of FIG. 9, three longitudinal elements 54 are shown in this example, but more or fewer longitudinal elements 54 may be used. The longitudinal elements 54 and expansion rings 56 may be any suitable size or shape and need not be circular in cross-section. For example, the cross-sectional shape of the longitudinal elements 54 and/or expansion rings 56 may be oval, rectangular, square, or another suitable shape.

Similar to the tubes as described with respect to FIGS. 1-3, the expandable structure 52 may be coated with, or may otherwise carry, a therapeutic agent. In this manner, when the expandable structure 52 is deployed to its expanded configuration as shown in FIG. 11 against the vessel wall, the therapeutic agent can be delivered to the vessel wall.

In certain situations, it may be desirable to utilize a drug delivery sheath 60 located on the outside of the drug delivery extension. In the example of FIGS. 8-11, a drug delivery sheath 60 may be located on the outside of the expandable structure 52 (the sheath 60 is not shown in FIGS. 9 and 10).

The therapeutic agent can be located on the sheath 60, such that when the drug delivery extension is deployed, the drug is delivered from the sheath 60 to the vessel wall. That is, when the sheath 60 is expanded to contact the vessel wall, the drug elutes from the sheath 60 to the vessel wall.

A medical device 13 such as that shown in FIGS. 8-11 may be used in the following manner. The balloon 20, in its collapsed configuration, is delivered to a constriction in the vessel. Techniques such as those known in the art can be used to position the balloon at the desired site. Once the balloon 20 is at the constriction, the balloon 20 is expanded from its collapsed configuration to its expanded configuration. When sufficiently expanded, the outer surface 22 of the balloon 20 presses against the wall of the vessel for dilatation of the constriction. At or around this time, the drug delivery extension 50 is deployed to deliver the therapeutic agent to an area beyond the outer surface 22 of the balloon 20. In the example of FIGS. 8-11, in which the expandable structure 52 has a compression reservoir that is compressed when it is pressed by the balloon 20 against the wall of the vessel, the step of expanding the balloon 20 to cause the outer surface 22 of the balloon 20 to press against the wall of the vessel also compresses the compression reservoir and causes the deployment of the drug delivery extension 50.

An expandable structure such as expandable structure 52 may be expanded in other ways. For example, the expandable structure may be formed of a shape-memory material that is activated by heat. Alternatively, the expandable structure may be a self-expanding structure that is held in a sheath during delivery and released from the sheath for deployment. Similarly, the tubes and/or elongate members in other embodiments described herein may similarly be formed of shape-memory and activated by heat for deployment and/or otherwise constructed to be self-expanding.

The therapeutic agent used in embodiments of the present disclosure may be a pharmaceutically-acceptable agent such as a drug, a non-genetic therapeutic agent, a biomolecule, a small molecule, or cells. Example drugs include anti-proliferative agents or anti-restenosis agents such as paclitaxel, sirolimus (rapamycin), tacrolimus, everolimus, and zotarolimus.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl) ethyleneglycol-N,N,N',N'-tetraacetic acid and mixtures thereof; antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; structural protein (e.g., collagen) cross-link breakers such as alagebrium (ALT-711); and/or any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMPs"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, and BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds having a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin$^-$) cells including Lin$^-$CD34$^-$, Lin$^-$ CD34$^+$, Lin$^-$cKit$^+$, mesenchymal stem cells including mesenchymal stem cells with 5-aza, cord blood cells, cardiac or other tissue-derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells. Any of the therapeutic agents may be combined to the extent such combination is biologically compatible.

The foregoing description and examples have been set forth merely to illustrate the disclosure and are not intended to be limiting. Each of the disclosed aspects and embodiments of the present disclosure may be considered individually or in combination with other aspects, embodiments, and variations of the disclosure. Modifications of the disclosed embodiments incorporating the spirit and substance of the disclosure may occur to persons skilled in the art and such modifications are within the scope of the present disclosure.

What is claimed is:

1. A medical device for dilatation of a vessel and delivery of a therapeutic agent to a wall of the vessel, the medical device comprising:
   a catheter;
   a balloon located at a distal end of the catheter, the balloon having a collapsed configuration and an expanded configuration, the balloon having an outer surface configured to press against the wall of the vessel when the balloon is in its expanded configuration for dilatation of a constriction in the vessel; and
   a drug delivery extension configured to extend beyond the outer surface of the balloon when the balloon is in its expanded configuration in order to deliver the therapeutic agent to an area beyond the outer surface of the balloon;
   wherein when the drug delivery extension is extended, the drug delivery extension extends in a direction generally parallel to a longitudinal axis of the balloon, at least one of distally from a distal end of the balloon and proximally from a proximal end of the balloon.

2. A medical device according to claim 1,
   wherein the drug delivery extension comprises a tube having a rolled configuration and an unrolled configuration; and
   wherein when the tube is in its unrolled configuration, the tube extends beyond the outer surface of the balloon in order to deliver the therapeutic agent to the area beyond the outer surface of the balloon.

3. A medical device according to claim 2, further comprising a compression reservoir;
   wherein the compression reservoir is compressed to a compressed condition when the balloon is expanded to its expanded configuration and the outer surface of the balloon presses against the wall of the vessel; and
   wherein compression of the compression reservoir to its compressed condition causes the tube to unroll from its rolled configuration to its unrolled configuration.

4. A medical device according to claim 2,
   wherein the drug delivery extension comprises a plurality of tubes, each tube of the plurality of tubes having a rolled configuration and an unrolled configuration; and
   wherein when each tube of the plurality of tubes is in its unrolled configuration, each tube extends beyond the outer surface of the balloon in order to deliver the therapeutic agent to the area beyond the outer surface of the balloon.

5. A medical device according to claim 1,
   wherein the drug delivery extension comprises at least one elongate member having a collapsed configuration and an expanded configuration; and
   wherein when the at least one elongate member is in its expanded configuration, the at least one elongate member extends beyond the outer surface of the balloon in order to deliver the therapeutic agent to the area beyond the outer surface of the balloon.

6. A medical device according to claim 5,
   further comprising an actuation mechanism for deploying the at least one elongate member from its collapsed configuration to its expanded configuration.

7. A medical device according to claim 5,
   wherein the drug delivery extension comprises a plurality of elongate members, each having a collapsed configuration and an expanded configuration; and
   wherein when each of the elongate members of the plurality of elongate members is in its expanded configuration, each of the elongate members extends beyond the outer surface of the balloon in order to deliver the therapeutic agent to the area beyond the outer surface of the balloon.

8. A medical device according to claim 1,
   wherein the drug delivery extension comprises an expandable structure having a collapsed configuration and an expanded configuration; and
   wherein when the expandable structure is in its expanded configuration, the expandable structure extends beyond the outer surface of the balloon in order to deliver the therapeutic agent to the area beyond the outer surface of the balloon.

9. A medical device according to claim 8, further comprising a compression reservoir;
   wherein the compression reservoir is compressed to a compressed condition when the balloon is expanded to its expanded configuration and the outer surface of the balloon presses against the wall of the vessel; and
   wherein compression of the compression reservoir to its compressed condition causes the expandable structure to expand from its collapsed configuration to its expanded configuration.

10. A medical device according to claim 9,
    wherein the expandable structure comprises a plurality of tubes; and
    wherein the compression reservoir comprises a portion of the tubes located on the outer surface of the balloon.

11. A medical device according to claim 1, wherein the therapeutic agent is located on an outside of the drug delivery extension.

12. A medical device according to claim 1, wherein the therapeutic agent is located inside a lumen of the drug delivery extension and is forced out of openings in the drug delivery extension when the drug delivery extension is extended.

13. A medical device according to claim 1,
    further comprising a drug delivery sheath located on an outside of the drug delivery extension;
    wherein the therapeutic agent is located on the sheath; and wherein when the drug delivery extension is extended, the therapeutic agent is delivered from the sheath to the vessel wall.

14. A method for dilatation of a vessel and delivery of a therapeutic agent to a wall of the vessel, the method comprising:
   using a medical device comprising:
      a catheter;
      a balloon located at a distal end of the catheter, the balloon having a collapsed configuration and an expanded configuration, the balloon having an outer surface configured to press against the wall of the vessel when the balloon is expanded to its expanded configuration for dilatation of a constriction in the vessel; and
      a drug delivery extension configured to extend beyond the outer surface of the balloon when the balloon is in its expanded configuration in order to deliver the therapeutic agent to an area beyond the outer surface of the balloon;
   delivering the balloon to the constriction in the vessel;
   expanding the balloon from its collapsed configuration to its expanded configuration such that the outer surface of the balloon presses against the wall of the vessel for dilatation of the constriction; and
   deploying the drug delivery extension to deliver the therapeutic agent to the area beyond the outer surface of the balloon;
   wherein when the drug delivery extension is deployed, the drug delivery extension extends in a direction generally parallel to a longitudinal axis of the balloon, at least one of distally from a distal end of the balloon and proximally from a proximal end of the balloon.

15. A method according to claim 14,
   wherein the drug delivery extension comprises a tube having a rolled configuration and an unrolled configuration;
   wherein the step of deploying the drug delivery extension comprises unrolling the tube from its rolled configuration to its unrolled configuration; and
   wherein when the tube is in its unrolled configuration, the tube extends beyond the outer surface of the balloon in order to deliver the therapeutic agent to the area beyond the outer surface of the balloon.

16. A method according to claim 14,
   wherein the drug delivery extension comprises at least one elongate member having a collapsed configuration and an expanded configuration;
   wherein the step of deploying the drug delivery extension comprises expanding the at least one elongate member from its collapsed configuration to its expanded configuration; and
   wherein when the at least one elongate member is in its expanded configuration, the at least one elongate member extends beyond the outer surface of the balloon in order to deliver the therapeutic agent to the area beyond the outer surface of the balloon.

17. A method according to claim 14,
   wherein the drug delivery extension comprises an expandable structure having a collapsed configuration and an expanded configuration;
   wherein the step of deploying the drug delivery extension comprises expanding the expandable structure from its collapsed configuration to its expanded configuration; and
   wherein when the expandable structure is in its expanded configuration, the expandable structure extends beyond the outer surface of the balloon in order to deliver the therapeutic agent to the area beyond the outer surface of the balloon.

18. A medical device for dilatation of a vessel and delivery of a therapeutic agent to a wall of the vessel, the medical device comprising:
   a catheter;
   a balloon located at a distal end of the catheter, the balloon having a collapsed configuration and an expanded configuration; and
   a drug delivery extension attached to the balloon, the drug delivery extension having an undeployed configuration and a deployed configuration;
   wherein the drug delivery extension in its deployed configuration extends beyond an outer surface of the balloon;
   wherein the drug delivery extension comprises an expandable structure having a collapsed configuration and an expanded configuration;
   wherein when the expandable structure is in its expanded configuration, the expandable structure extends beyond the outer surface of the balloon in order to deliver the therapeutic agent to an area beyond the outer surface of the balloon;
   wherein the medical device further comprises a compression reservoir;
   wherein the compression reservoir is compressed to a compressed condition when the balloon is expanded to its expanded configuration and the outer surface of the balloon presses against the wall of the vessel; and
   wherein compression of the compression reservoir to its compressed condition causes the expandable structure to expand from its collapsed configuration to its expanded configuration.

19. A medical device according to claim 18, wherein when the drug delivery extension is deployed, the drug delivery extension extends in a direction generally parallel to a longitudinal axis of the balloon, at least one of distally from a distal end of the balloon and proximally from a proximal end of the balloon.

20. A medical device according to claim 18, wherein when the drug delivery extension is deployed, the drug delivery extension extends away from the outer surface of the balloon in a direction extending away from a longitudinal axis of the balloon.

* * * * *